United States Patent [19]

Fisher

[11] Patent Number: 5,500,016
[45] Date of Patent: Mar. 19, 1996

[54] ARTIFICIAL HEART VALVE

[75] Inventor: John Fisher, Yorkshire, United Kingdom

[73] Assignee: University of Leeds, Yorkshire, United Kingdom

[21] Appl. No.: 307,623

[22] PCT Filed: Mar. 19, 1993

[86] PCT No.: PCT/GB93/00568

§ 371 Date: Sep. 20, 1994

§ 102(e) Date: Sep. 20, 1994

[87] PCT Pub. No.: WO93/18721

PCT Pub. Date: Sep. 30, 1993

[30] Foreign Application Priority Data

Mar. 25, 1992 [GB] United Kingdom .................... 9206449

[51] Int. Cl.$^6$ ..................................................... A61F 2/24
[52] U.S. Cl. ............................................................. 623/2
[58] Field of Search ........................................ 623/2, 900

[56] References Cited

U.S. PATENT DOCUMENTS

| 15,192 | 6/1856 | Peale | 623/2 |
|---|---|---|---|
| 3,320,972 | 5/1967 | High et al. | |
| 4,624,822 | 11/1986 | Arru et al. | 623/2 |
| 4,629,459 | 12/1986 | Ionescu et al. | 623/2 |
| 4,778,461 | 10/1988 | Pietsch et al. | 623/2 |
| 4,888,009 | 12/1989 | Le Derman et al. | 623/2 |
| 5,258,023 | 11/1993 | Reger | 623/2 |

FOREIGN PATENT DOCUMENTS

| 1232407 | 2/1988 | Canada . | |
|---|---|---|---|
| 0114025 | 7/1984 | European Pat. Off. . | |
| 0193987 | 9/1986 | European Pat. Off. | 632/2 |
| 0515324 | 11/1992 | European Pat. Off. | 623/2 |
| 0582800 | 12/1977 | U.S.S.R. | 623/2 |
| 0990215 | 1/1983 | U.S.S.R. | 623/2 |
| 1443221 | 7/1976 | United Kingdom . | |
| 2255394 | 11/1992 | United Kingdom | 623/2 |
| 92/12690 | 8/1992 | WIPO . | |

OTHER PUBLICATIONS

Ghista, D. N., "Toward An Optimum Prosthetic Trileaflet Aortic–Valve Design", *Medical And Biological Engineering*, vol. 14, No. 2, Mar. 1976, London, U.K., pp. 122–129.

Primary Examiner—David H. Willse
Assistant Examiner—Bruce E. Snow
Attorney, Agent, or Firm—Sughrue, Mion, Zinn, Macpeak & Seas

[57] ABSTRACT

A flexible leaflet heart valve (1), to replace natural aortic or pulmonary valves of the heart, includes a frame (3) and flexible leaflets (2) attached to the frame (3). Each flexible leaflet (2) forms part of a surface of revolution having its axis of revolution substantially orthogonal to the direction of blood flow through the valve (1). The valve (1) has improved opening characteristics under low flow conditions, and allows a large range of geometries for the same size valve.

9 Claims, 2 Drawing Sheets

ARTIFICIAL HEART VALVE

BACKGROUND OF THE INVENTION

The present invention relates to artificial heart valves, and more particularly to flexible leaflet heart valves which are used to replace the natural aortic or pulmonary valves of the heart.

Conventionally, ball or disk valves are used to replace natural mitral or tricuspid aortic or pulmonary valves of the heart. These artificial valves comprise a rigid frame defining an aperture and a cage enclosing a ball or a disk. When blood flows in the desired direction, the ball or disk lifts away from the frame allowing the blood to flow through the aperture. The ball or disk is restrained by the cage by struts or by a pivot. When blood tries to flow in the reverse direction, the ball or disk becomes seated over the aperture and prevents the flow of blood through the valve. The disadvantage of these valves is that the ball or disk remains in the blood stream when the blood flows in the desired direction, and this causes a disturbance to blood flow.

More recently, flexible leaflet valves have been proposed which mirror natural heart valves more closely. These valves have a generally rigid frame and flexible leaflets attached to this frame. The leaflets are arranged so that, in the closed position, each leaflet contacts its neighbour thereby closing the valve and preventing the flow of blood. In the open position, the leaflets separate from each other, and radially open out towards the inner walls of an artery in which the valve is located. The leaflets are either made from chemically treated animal tissue or polyurethane material. The leaflets must be capable of withstanding a high back pressure across the valve when they are in the closed position, yet must be capable of opening with the minimum pressure across the valve in the forward direction. This is necessary to ensure that the valve continues to correctly operate even when the blood flow is low, and to ensure that the valve opens quickly when blood flows in the desired direction.

A wide range of geometries are used to describe natural aortic valve leaflets during diastole, but these geometries cannot be used for valves made from pericardial or synthetic materials due to the approximately isotropic properties of such materials compared to the highly anistropic material of the natural valve. Consequently, different geometries have to be used to form flexible leaflet heart valves made from pericardial or synthetic materials with isotropic mechanical properties.

Conventional flexible leaflet heart valves have three substantially identical leaflets mounted onto the frame. The leaflets have a range of designs, both in the geometry of the leaflet and the variations in thickness of the leaflets. Original flexible leaflet heart valves incorporate leaflets which are spherical or conical when in the relaxed state, that is when no pressure is acting on the leaflet. More recently, cylindrical and ellipsoidal leaflets have been proposed. These leaflet geometries are formed with an axis of revolution in a plane generally parallel to the blood flow through the valve.

DISCLOSURE OF THE INVENTION

According to the present invention, a flexible leaflet heart valve for controlling the flow of blood comprises a substantially rigid frame and a plurality of substantially identical flexible leaflets mounted on the frame, characterised in that each flexible leaflet forms part of a surface of revolution having its axis of revolution lying in a plane substantially orthogonal to the direction of blood flow through the valve, and a shape defined by the equation:

$$z^2+y^2=2R_L(x-g)-\alpha(x-g)^2$$

where:

g is the offset of the leaflet from the axis of the frame;

$R_L$ is the radius of curvature of the leaflet at $(g,0,0)$; and $\alpha$ is the shape parameter and is greater than 0 and less than 1.

A flexible leaflet valve according to the present invention has improved opening characteristics under low flow conditions. The shape of the leaflets is such that the radius of curvature of the leaflet continuously increases in two directions away from the centre point of the free edge. By varying the radius of curvature, the leaflet shape may be varied and still fit within the frame.

The value of $\alpha$ may be in the range of 0.2 to 0.8, but is preferably in the range 0.4 to 0.6, and more preferably is about 0.5.

Preferably, x is in the range of 0 to $R_L$, y is in the range between $-R_L$ and $+R_L$, and z lies in the range $-1.8\ R_L$ to $+0.2\ R_L$.

The valve preferably includes three leaflets, and in this case the valve closure is preferably effected by the surface adjacent the free edge of each leaflet making sealing contact with the two neighbouring leaflets. The frame on which the leaflets are mounted is preferably circular in cross-section, and has a size dependent upon the size of the aorta or pulmonary artery in which the valve is to be used.

Preferably, each leaflet is made from a polyurethane material, and has a variable thickness, preferably between 0.15 mm and 0.25 mm.

BRIEF DESCRIPTION OF THE DRAWINGS

An example of a flexible leaflet heart valve according to the present invention will be described with reference to the accompanying drawings, in which.

DESCRIPTION OF PREFERRED EMBODIMENT

Figure 1:
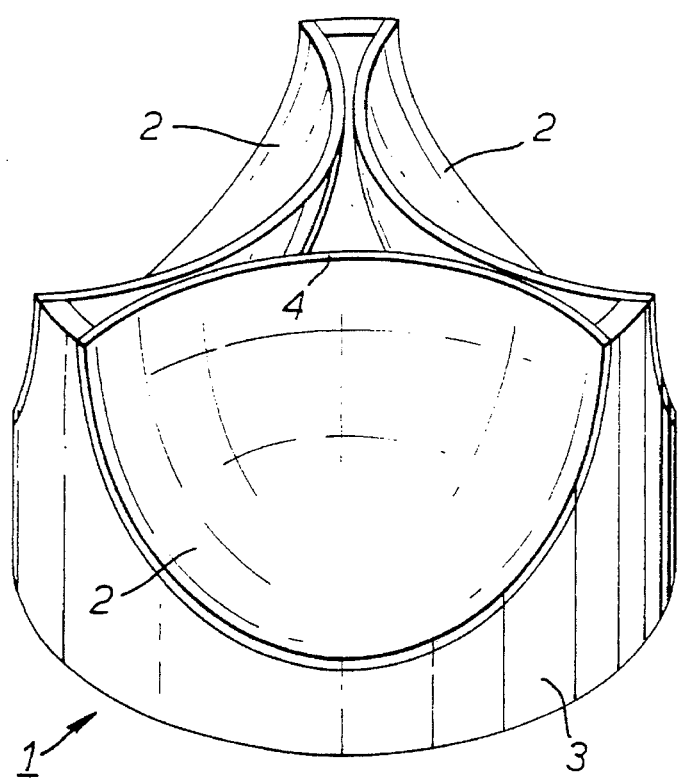
FIG. 1 shows an overall view of the valve.

As shown in FIG. 1, a flexible leaflet heart valve 1 includes three flexible leaflets 2 which are substantially identical to each other. The leaflets 2 have a free edge 4. The leaflets 2 are mounted symmetrically on a frame 3. The valve 1 is positioned in an artery with the axis of the frame 3 generally co-axial to the axis of the artery, and hence in the same direction as the blood flow along the artery. The leaflets 2 form part of a paraboloid having its axis of revolution lying in a plane orthogonal to the direction of blood flow.

Figure 2:
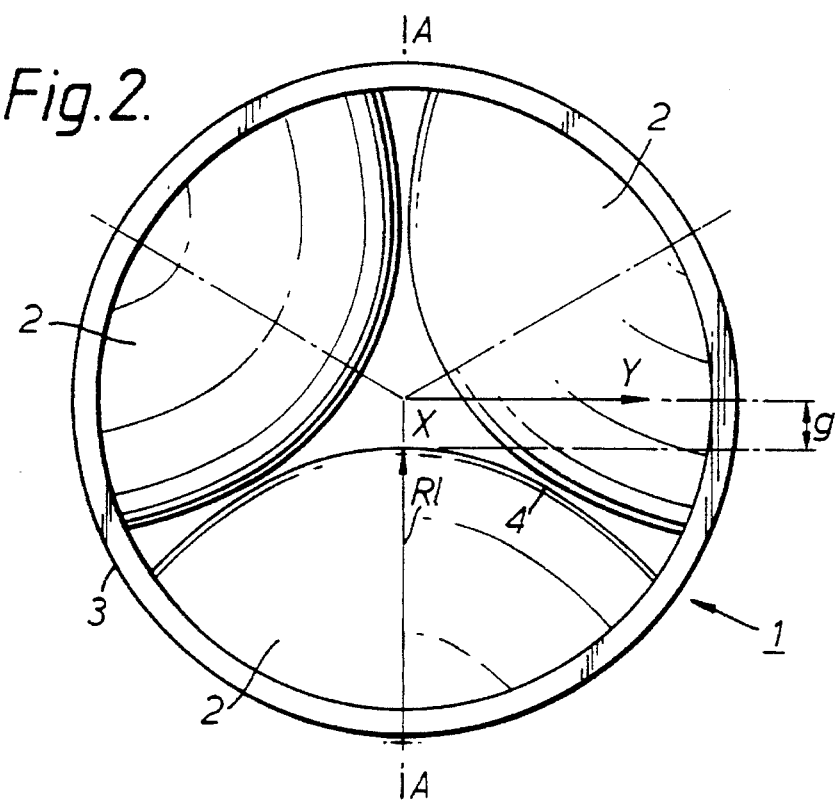
FIG. 2 shows a plan of the valve.
Figure 3:
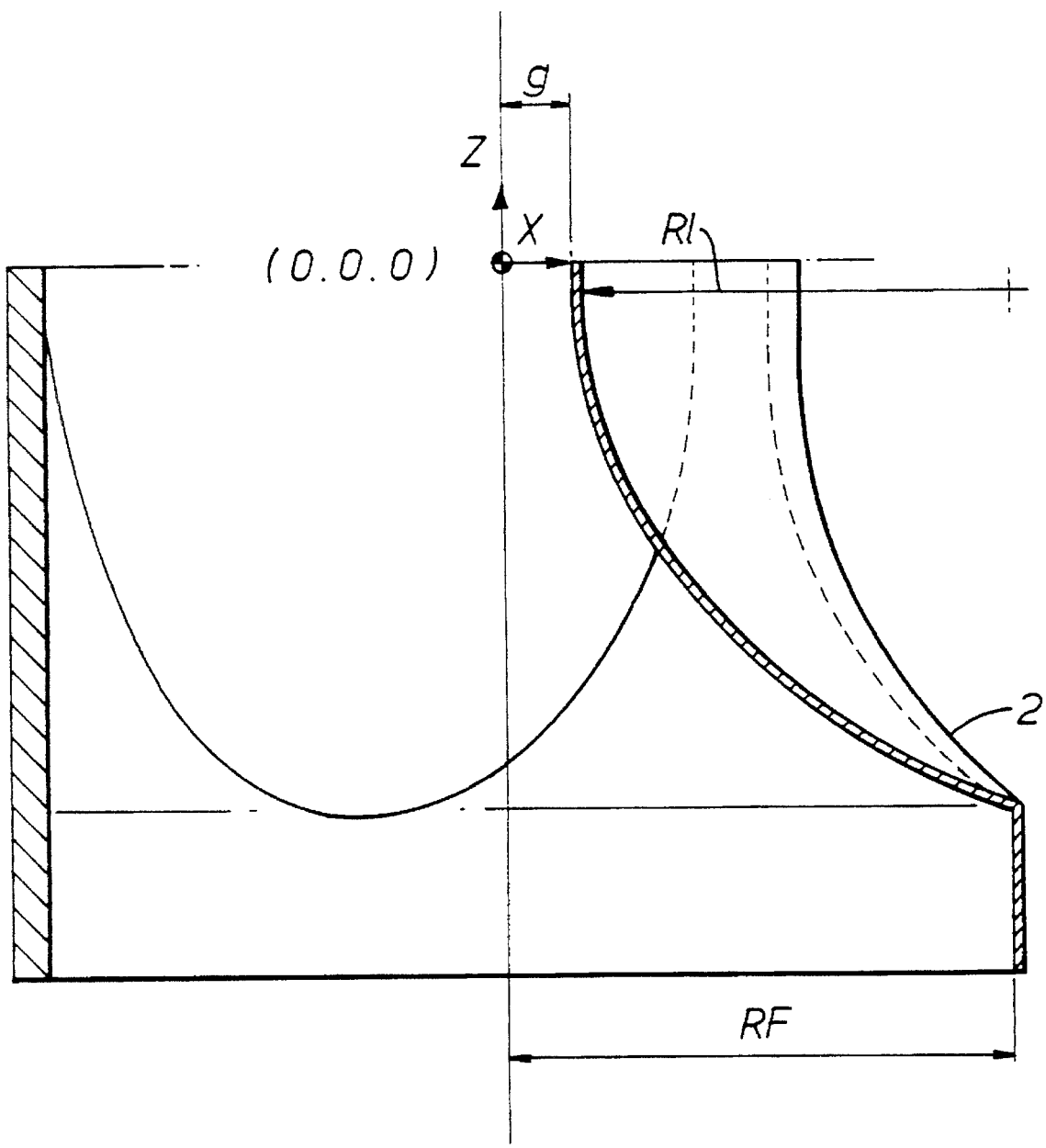
FIG. 3 shows a cross section of one leaflet of the valve taken along the line A—A shown in FIG. 2.

Using cartesian geometry with the z direction being the direction of blood flow, the y direction orthogonal to this and extending from the centre of the free edge 4 of the leaflet 2, and the x direction being orthogonal to both the y and z directions, then the shape of the leaflet is represented by the equation:

$$z^2+y^2=2R_L(x-g)-\alpha(x-g)$$

where:

g is the offset of the leaflet from the axis of the frame as shown in FIG. 3;

$R_L$ is the radius of curvature of the leaflet at (g, 0, 0) as shown in FIG. 2; and α is the shape parameter, and is greater than 0 and less than 1.

If α=1 the geometry of the leaflet 2 will be spherical. When α=0, the surface will be parabolic. However, for 0>α>1, the leaflet shape has a variable radius of curvature having its axis of revolution in the x, y plane. This allows leaflets to be produced having a shape to give the required properties which also fits within any given frame.

The valve radius, $R_F$ as shown in FIG. 3, and $R_L$ are both in the range of 5 mm to 20 mm, g is in the range of 0 to 3 mm and α is 0.5.

Leaflets of this shape open radially away from the centre of the frame out towards the wall of the artery with a very low pressure, typically below 1 mm Hg. This is important as if the valve 1 fails to open at low pressures, the blood will cease to circulate. The shape of the leaflets 2 also ensures that they rapidly close when the blood tries to flow in the reverse direction, therefore quickly preventing the blood from flowing in this direction.

Various sizes of frame 3 may be used depending upon the size of the artery. Due to the leaflets 2, a frame radius $R_F$ of about 13.5 mm produces a valve having an effective orifice area of approximately 2.5 cm². This typically allows approximately 4.5 liters per minute of blood to flow through, at which rate, the valve 1 has a closing regurgitant volume of less than 3 ml per stroke.

Although not shown, the valve may have only two or more than three flexible leaflets 2.

The precise size and shape of the leaflets 2 depends upon the particular size of vessel in which the valve 1 is to be used. In particular, the shape parameter α of the leaflets 2, may be varied to produce a set of valves 1 of substantially the same size but different shapes to suit most applications. Alternatively, a set of heart valves 1 may be produced all of which have the same shape, but have different sizes for particular applications.

I claim:

1. A flexible leaflet heart valve for controlling the flow of blood in an artery comprising a substantially rigid frame (3), and a plurality of substantially identical flexible leaflets (2) mounted on the frame (3), characterised in that each flexible leaflet (2) is formed from part of a surface of revolution having its axis of revolution lying in a plane substantially orthogonal to the direction of blood flow through the valve (1), and a shape defined by the equation:

$$z^2+y^2=2R_L(x-g)-\alpha(x-g)^2$$

where:

g is the offset of the leaflet from the axis of the frame;

$R_L$ is the radius of curvature of the leaflet (2) at (g, 0, 0); and

α is the shape parameter and is greater than 0 and less than 1.

2. A flexible leaflet heart valve according to claim 1, in which α is in the range 0.2 to 0.8.

3. A flexible leaflet heart valve according to claim 2, in which α is within the range 0.4 to 0.6.

4. A flexible leaflet heart valve according to claim 3, in which α is substantially 0.5.

5. A flexible leaflet heart valve according to claim 1, in which x is in the range 0 to $R_L$, y, when present, is in the range $-R_L$ to $+R_L$, and z is in the range $-1.8 R_L$ to $+0.2 R_L$.

6. A flexible leaflet heart valve according to claim 1, in which $R_F$, which is a radius of the frame of the valve, and $R_L$ are both between 5 mm and 20 mm, and g is in the range 0 to 3 mm.

7. A flexible leaflet heart valve according to claim 1 including three flexible leaflets (2).

8. A flexible leaflet heart valve according to claim 1, in which the rigid frame (3) has a substantially circular cross section.

9. A flexible leaflet heart valve according to claim 1, in which the leaflets are made from polyurethane and have a variable thickness in the range 0.15 mm to 0.2 mm.

\* \* \* \* \*